United States Patent [19]

Tappe

[11] 4,342,688
[45] Aug. 3, 1982

[54] PROCESS FOR THE MANUFACTURE OF AN N-HYDROXYALKYLCARBAZOLE

[75] Inventor: Horst Tappe, Dietzenbach, Fed. Rep. of Germany

[73] Assignee: Cassella Aktiengesellschaft, Frankfurt (M) Fechenheim, Fed. Rep. of Germany

[21] Appl. No.: 244,910

[22] Filed: Mar. 18, 1981

[30] Foreign Application Priority Data

Mar. 27, 1980 [DE] Fed. Rep. of Germany ....... 3011808

[51] Int. Cl.³ .......................................... C07D 209/86
[52] U.S. Cl. .................................................. 260/315
[58] Field of Search ........................................ 260/315

[56] References Cited

U.S. PATENT DOCUMENTS 3,014,918 12/1961 Dressler .............................. 260/315
3,894,041 7/1975 Otsuki et al. ....................... 260/315
3,944,565 3/1976 Otsuki et al. ....................... 260/315

Primary Examiner—Robert W. Ramsuer
Attorney, Agent, or Firm—Connolly and Hutz

[57] ABSTRACT

The process for manufacture of an N-hydroxyalkylcarbazole of the formula

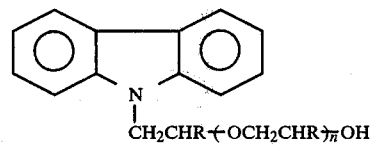

wherein R is H, $CH_3$ or $C_2H_5$ and n is a number from 0 to 4 which comprises reacting carbazole with an epoxide of the formula

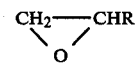

or a chlorohydrin of the formula

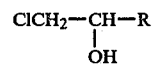

at temperatures from 20° to 150° C. in the presence of a base and a phase transfer catalyst, in an organic solvent which is immiscible with water.

10 Claims, No Drawings

PROCESS FOR THE MANUFACTURE OF AN N-HYDROXYALKYLCARBAZOLE

The invention relates to a process for the manufacture of an N-hydroxyalkylcarbazole of the formula I

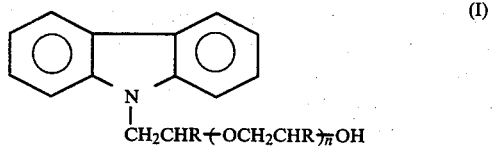

wherein R denotes H, $CH_3$ or $C_2H_5$ and n denotes a number from 0 to 4. R preferably denotes H.

N-$\beta$-Hydroxyethylcarbazole is an important starting product, for example for the polymerisation of vinylcarbazole to give polyvinylcarbazole. Polyvinylcarbazole which is used as a photoconductor in electrophotography has particularly good properties if the vinylcarbazole used for its polymerisation has been obtained by dehydrating N-$\beta$-hydroxyethylcarbazole. N-$\beta$-hydroxyethylcarbazole is also suitable for use as a coupling component for the manufacture of azo dyestuffs (U.S. Pat. No. 3,787,178).

Many processes for the preparation of N-$\beta$-hydroxyethylcarbazole by oxethylating carbazole with ethylene oxide or ethylene chlorohydrin have already been described. These reactions frequently require long reaction times of, for example, 26 to 30 hours in ketone solvents, such as, for example, acetone (British Patent Specification No. 620,733; J. Amer. Chem. Soc. 70, 3019 (1948). The isolation of the product in these reactions often requires involved extraction and crystallisation processes in which the solvent is frequently destroyed. In the absence of ketones the oxethylation of carbazole takes place with only minimal yields of, for example, 2% (C.A. 63, 565 (1965)). In other processes, the salts of carbazole have first to be prepared at high temperatures or using strong and expensive bases, and these salts in turn have to be reacted with 2-chloroethanol or ethylene oxide in the presence of ketones or high-boiling ethers to give the desired product. (CA 63, 565 (1965), German Offenlegungsschrift 2,354,326 and CA 81, 25550 (1974)).

In other processes the reaction is carried out using expensive solvents, such as dimethyl sulphoxide (French Patent Specification No. 1,527,778), which are subsequently diluted further with water and are thus lost or can only be regenerated with difficulty and expense.

There has therefore been an urgent need for a simple process for the oxalkylation of carbazole.

It has now been found, surprisingly, that, contrary to the teachings of CA 63, 565 (1965), carbazole can be oxalkylated very easily in good yields. The process according to the invention for the manufacture of an N-hydroxyalkylcarbazole of the formula I is characterized in that carbazole is reacted with an epoxide of the formula II or a chlorohydrin of the formula III

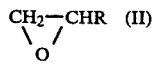 (II)    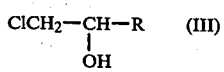 (III)

at temperatures from 20° to 150° C. in the presence of a base and a phase transfer catalyst, in an organic solvent which is immiscible with water.

The process according to the invention is carried out by allowing the reactants to react with one another under the reaction conditions according to the invention, indicated above, in a multi-phase system consisting of a liquid, non-aqueous phase and one or more solid phase. Thus, it is, for example, possible in principle to mix all the required components of the reaction mixture from the beginning in the required ratios, provided that suitable measures are taken to ensure that the reaction proceeds without difficulties, that is to say care must be taken in this case to ensure adequate removal of heat and, in the case of gaseous starting materials, to ensure liquefaction, as the result of a sufficiently high pressure.

In order to avoid from the outset difficulties in carrying out the reaction, an embodiment of the process according to the invention will, as a rule, be chosen in which the initial products taken are the carbazole, dissolved or undissolved, and the base, undissolved in a system consisting of solvent and phase transfer catalyst, and the epoxide or chlorohydrin is then metered in.

Compounds having different values for n can be obtained by varying the molar ratio carbazole:epoxide or chlorohydrin. In the case of the carbazole:epoxide (epoxides of the formula II, particularly ethylene oxide, are preferably used) molar ratios indicated in the table which follows, the values indicated for n are theoretically obtained in the compound I:

| Molar ratio Carbazole:Epoxide | n |
|---|---|
| 1:1 | 0 |
| 1:2 | 1 |
| 1:3 | 2 |
| 1:4 | 3 |
| 1:5 | 4 |

When carrying out the process in practice, mixtures of compounds of the formula I having differing values of n can be formed at carbazole:epoxide (or halogenohydrin) molar ratios of 1:($>$1); this is even advantageous for various end uses, for example when the product is used as a coupling component.

The water-immiscible organic solvents used are aliphatic or aromatic hydrocarbons, which can also be halogenated. Solvents which are liquid at normal temperature will normally be used. Mixtures of different solvents can also be used. Examples of suitable solvents are pentane, hexane, heptane, octane, nonane, decane, petroleum ether, ligroin, light naphtha and heavy naphtha, benzene, alkylbenzenes having 1 to 3 alkyl radicals, preferably methyl radicals, such as, for example, toluene, ortho-, meta- or para-xylene, ethylbenzene, diethylbenzene or isopropylbenzene and halogenobenzenes or halogenoalkylbenzenes containing 1 to 3 halogens, particularly chlorine substituents, such as, for example, monochlorobenzene, ortho-, meta- or para-dichlorobenzene and ortho-, meta- or para-chlorotoluene.

It is preferable to use a solvent or solvent mixtures having boiling points between 50° and 180° C. Toluene or monochlorobenzene are preferred as the solvent. Nor is the smooth progress of the process according to the invention impaired in a disadvantageous manner by the carbazole or the base used being very slightly soluble in the solvent or mixture of solvents employed.

The bases employed are compounds which are capable of effecting an equilibrium conversion of the carbazole at least partly into its anion. Examples of bases of this type are alkali metal hydroxides or alkali metal hydrides.

It is preferable to use potassium hydroxide or sodium hydroxide, particularly in a powdered form. Mixtures of different bases can also be used. The quantity of the base to be employed is appropriately 1 to 3 mols per mol of carbazole.

The quantity of the phase transfer catalyst to be employed is appropriately 2 to 20 mol %, relative to the quantity of carbazole. It is preferable to employ 4 to 15 mol %, particularly 10 to 15 mol %, of the phase transfer catalyst. A summarising review of suitable phase transfer catalysts is to be found, for example, in the book by W. P. Weber and G. W. Gokel, Phase Transfer Catalysis in Organic Synthesis, Springer Verlag, Berlin and New York 1977. Suitable phase transfer catalysts for carrying out the process according to the invention are particularly quaternary ammonium salts of the formula IV

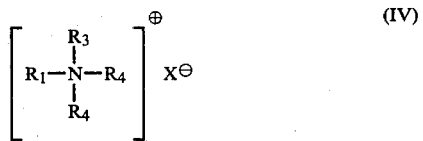

in which $R_1$ to $R_4$ denote alkyl having 1 to 18 C atoms, alkylphenyl having 1 to 10 C atoms in the alkyl radical, benzyl and phenethyl and $X^-$ denotes the ions $Cl^-$, $Br^-$, $SO_4^{--}$ and $HSO_4^-$, and also crown ethers and optionally etherified polyethylene glycol derivatives, for example polyethylene glycol dimethyl ethers having molecular weights of, for example, up to 600. Crown ethers are preferred. Etherified polyethylene glycol derivatives and etherified copolymers formed from ethylene oxide and tetrahydrofuran are particularly preferred.

Examples of suitable phase transfer catalysts of the formula IV are di-(dodecyl)-dimethylammonium chloride, hexadecyltrimethylammonium chloride, tetrabutylammonium chloride, trioctylmethylammonium chloride, tris-decylmethylammonium chloride and trialkyl-($C_8$–$C_{10}$ mixture)-methylammonium chloride. Examples of suitable crown ethers are dicyclohexano[18]-crown-6, [18]crown-6, [15]crown-5 and dibenzo[18]crown-6.

The process according to the invention is carried out at temperatures between 20° and 180° C. The temperature range from 60° to 135° C. is particularly advantageous, preferably the range from 80° to 120° C. It is appropriate to carry out the reaction in the absence of water.

Examples of compounds of the formulae II and III are ethylene oxide, propylene oxide and 2-chloroethanol. Ethylene oxide is used preferentially.

After the completion of the reaction, the reaction batches are worked up in a manner which is in itself known. The base present in the reaction batches is appropriately removed by adding water and separating off the aqueous phase. The organic solvent then only contains the end product, which can easily be obtained in a pure state by processes which are in themselves known, such as, for example, distillation. The removal of the organic solvent by distillation can be effected under normal pressure or under reduced pressure or by means of steam distillation.

The process according to the invention makes it possible to manufacture compounds which are of high value, for example as intermediate products for organic synthesis, in high yields and in a very good state of purity in a manner which is technically particularly simple and unobjectionable from the ecological point of view. In regard to these characteristics the process is considerably superior to the nearest comparable processes. In particular, the troublesome and expensive preparation of the alkali metal salt of carbazole is obviated by the process according to the invention. Thus the β-hydroxyethylcarbazole prepared by the process according to the invention only has a slightly yellowish colour, while yellow-brown to black compounds are obtained by the known process.

In the following illustrative embodiments all the parts are parts by weight and all the percentages are percentages by weight.

EXAMPLE 1

1 l of toluene, 167 g (1 mol) of carbazole, 60 g of NaOH powder and 40 g of pentaethylene glycol dimethyl ether are put into a 2-liter four-necked flask.

The mixture is stirred for 1 hour at 110° C. and cooled to 85° C. and 1.1 mols of ethylene oxide are passed in during the course of 1 hour, while stirring. When the reaction is complete, the mixture is cooled to 20° C., 800 ml of water are added, the aqueous phase is separated off in a separation funnel and the organic phase is washed with water and then distilled. The toluene is distilled off first under normal pressure and the N-β-hydroxyethylcarbazole is then distilled off under reduced pressure at 206° to 210° C./2 mm Hg.

Yield: 194 g of N-β-hydroxyethylcarbazole in the form of a slightly yellow product.

EXAMPLE 2

Example 1 is repeated, but employing 30 g of a mixed polyglycol dimethyl ether, prepared from tetrahydrofuran, ethylene oxide and methyl chloride (5 mols of ethylene oxide, 1 mol of tetrahydrofuran and 2 mols of methyl chloride are used per mol).

Yield: 187 g of N-β-hydroxyethylcarbazole.

What is claimed is:

1. The process for manufacturer of an N-hydroxyalkylcarbazole of the formula

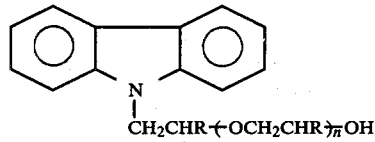

wherein R is H, $CH_3$ or $C_2H_5$ and n is a number from 0 to 4 which comprises reacting carbazole with an epoxide of the formula

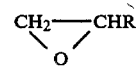

or a chlorhydrin of the formula

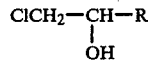

at temperatures from 20° to 150° C. in the presence of a base and a phase transfer catalyst, in an organic solvent which is immiscible with water.

2. The process according to claim 1 wherein the reaction is carried out in the absence of water.

3. The process according to claims 1 or 2 wherein the base is an alkali metal hydroxide.

4. The process according to claim 3 wherein the base is sodium hydroxide or potassium hydroxide.

5. The process according to claim 1 wherein relative to carbazole, the phase transfer catalyst amounts to 2 to 20 mole percent.

6. The process according to claim 5 wherein relative to carbazole, the phase transfer catalyst amounts to 10 to 15 mole percent.

7. The process according to claim 1 where the reaction is carried out at 60° to 120° C.

8. The process according to claim 7 wherein the reaction is carried out at 80° to 120° C.

9. The process according to claim 1 wherein the phase transfer catalyst is a glycol ether, a crown ether or a quaternary ammonium salt of the formula

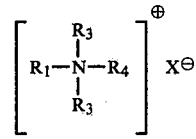

wherein $R_1$ to $R_4$ are each alkyl having 1 to 18 carbon atoms, alkylphenyl having 1 to 10 carbon atoms in the alkyl moiety, benzyl or phenethyl and $X^\ominus$ is the ion $Cl^-$, $Br^-$, $SO_4^{--}$ or $HSO_4^-$.

10. The process according to claim 1 wherein the reaction solvent is petroleum ether, ligroin, benzene, toluene, chlorobenzene, dichlorobenzene or chlorotoluene.

* * * * *